(12) United States Patent
Yoshizawa et al.

(10) Patent No.: US 10,426,778 B2
(45) Date of Patent: Oct. 1, 2019

(54) PROPHYLACTIC AGENT AND/OR THERAPEUTIC AGENT FOR DIFFUSE LARGE B-CELL LYMPHOMA

(71) Applicant: ONO PHARMACEUTICAL CO., LTD., Osaka (JP)

(72) Inventors: Toshio Yoshizawa, Osaka (JP); Ryohei Kozaki, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/167,835

(22) Filed: Oct. 23, 2018

(65) Prior Publication Data

US 2019/0054091 A1 Feb. 21, 2019

Related U.S. Application Data

(62) Division of application No. 15/208,998, filed on Jul. 13, 2016, now Pat. No. 10,137,129, which is a division of application No. 14/666,496, filed on Mar. 24, 2015, now Pat. No. 9,416,131.

(30) Foreign Application Priority Data

Mar. 25, 2014 (JP) ................. 2014-061413

(51) Int. Cl.
| C07D 473/34 | (2006.01) |
| A61K 31/522 | (2006.01) |
| A61P 35/00 | (2006.01) |
| A61K 45/06 | (2006.01) |

(52) U.S. Cl.
CPC ............ *A61K 31/522* (2013.01); *A61K 45/06* (2013.01); *A61P 35/00* (2018.01); *C07D 473/34* (2013.01)

(58) Field of Classification Search
None
See application file for complete search history.

(56) References Cited

U.S. PATENT DOCUMENTS

| 7,071,199 B1 | 7/2006 | Hirst et al. |
| 8,557,803 B2 | 10/2013 | Yamamoto et al. |
| 8,940,725 B2 | 1/2015 | Yamamoto et al. |
| 2003/0171360 A1 | 9/2003 | Gross et al. |
| 2008/0076921 A1 | 3/2008 | Honigberg et al. |
| 2013/0079327 A1 | 3/2013 | Yamamoto et al. |
| 2013/0217880 A1 | 8/2013 | Yamamoto et al. |
| 2014/0303191 A1 | 10/2014 | Buggy et al. |
| 2014/0330015 A1 | 11/2014 | Yamamoto et al. |
| 2015/0118222 A1 | 4/2015 | Levy et al. |
| 2015/0125446 A1 | 5/2015 | Klein et al. |
| 2015/0274730 A1 | 10/2015 | Yoshizawa et al. |

FOREIGN PATENT DOCUMENTS

| CA | 2800523 | 12/2011 |
| CA | 2857150 | 6/2013 |
| JP | 10-77271 | 3/1998 |
| JP | 2003-509427 | 3/2003 |
| JP | 2010-504324 | 2/2010 |
| WO | 2003/037890 | 5/2003 |
| WO | 2005/011597 | 2/2005 |
| WO | 2007/142755 | 12/2007 |
| WO | 2008/060301 | 5/2008 |
| WO | 2008/121742 | 10/2008 |
| WO | 2010/009342 | 1/2010 |
| WO | 2011/018224 | 2/2011 |
| WO | 2011/152351 | 12/2011 |
| WO | 2013/081016 | 6/2013 |
| WO | 2014/081712 | 5/2014 |
| WO | 2014/168975 | 10/2014 |
| WO | 2014/194254 | 12/2014 |
| WO | 2015/193740 | 12/2015 |
| WO | 2016/024228 | 2/2016 |
| WO | 2016/024230 | 2/2016 |

OTHER PUBLICATIONS

Meadows, Sarah. Blood (2012) vol. 119, No. 8.*
Yasuhiro et al., "ONO-4059, a novel oral Bruton's tyrosine kinase (Btk) inhibitor that demonstrates potent pharmacodynamic activity through Phosphorylated Btk (P-Btk) inhibition, in addition to effective anti-tumour activity in a TMD-8 (DLBCL) xenograft model", American Association for Cancer Research Annual Meeting 2013, Abstract No. 2452.
Rule et al., "A Phase I Study of the Oral Btk Inhibitor ONO-4059 in Patients With Relapsed/Refractory B -Cell Lymphoma", 55th American Society of Hematology, session: 624, program No. 4397, 2013.
Dyer et al., "The Bruton's tyrosine kinase (BTK) inhibitor ONO-4059: Single-agent activity in patients with relapsed and refractory non-GCB-DLBCL", 2014 ASCO Annual Meeting, Abstract No. 8553.
International Search Report dated Aug. 16, 2011 in International (PCT) Application No. PCT/ JP2011/062377.
Vetrie, David, et al., "The gene involved in X-linked agammaglobulinaemia is a member of the src family of protein-tyrosine kinases", Nature, vol. 361, Jan. 21, 1993, pp. 226-233.
Uckun, Fatih M., et al., "Bruton's Tyrosine Kinase as a New Therapeutic Target", Anti-Cancer Agents in Medicinal Chemistry, vol. 7, 2007, pp. 624-632.

(Continued)

*Primary Examiner* — Emily A Bernhardt
*Assistant Examiner* — Laura M Daniel
(74) *Attorney, Agent, or Firm* — Wenderoth, Lind & Ponack, L.L.P.

(57) ABSTRACT

To provide a medicament which shows more remarkable effect in treatment of activated B-cell like diffuse large B-cell lymphoma ABC-DLBCL than the existing Btk inhibitor, and is excellent in safety. The present compound exhibits more remarkable effect in treatment of activated B-cell like diffuse large B-cell lymphoma (ABC-DLBCL) patients, inter alia, ABC-DLBCL patients having CD79B wild-type gene background than the existing Btk inhibitor, and therefore, it can attain the object of the present invention.

7 Claims, No Drawings

(56) References Cited

OTHER PUBLICATIONS

Supplementary European Search Report dated Sep. 19, 2013 in European Application No. 11 78 9754.
Anderson, Chem. and Biol., vol. 10, 2003, pp. 787-797.
CAS RN 1222785810, entered STN May 13, 2010.
International Search Report dated Jan. 29, 2013 in International (PCT) Application No. PCT/JP2012/080769.
International Preliminary Report on Patentability and Written Opinion dated Jun. 3, 2014 in International (PCT) Application No. PCT/JP2012/080769.
International Search Report and Written Opinion dated Jun. 30, 2015 in corresponding International Application No. PCT/JP2015/001676.
Simon Rule et al., "*A Phase I Study of the Oral Btk Inhibitor ONO-4059 in Patients with Relapsed/Refractory B-Cell Lymphoma*", Blood Journal, 2013, vol. 122, Issue 21, p. 4397, Abstract #676.
Ryohei Kozaki et al., "*Development of a Bruton's Tyrosine Kinase (Btk) inhibitor-ONO-WG-307, a potential treatmentnt for B-cell malignancies*", Cancer Research, 2012, vol. 72, No. 8, Supp. 1, Abstract # 857.
R. Eric Davis et al., "*Chronic active B-cell-receptor signaling in diffuse large B-cell lymphoma*", Nature, 2010, vol. 463, pp. 88-92.
Byrn, Stephen, Solid-State Chemistry of Drugs, 2nd Ed. (1999), Ch. 11 Hydrates and Solvates, 233-247.
Morissette, Sherry, Adv. Drug Delivery Rev (2004), 56, 275-300.
Rouhi, A. M. Chem. & Eng. News (2003), 81 (8), 32-35.
Banker, Gilbert, Modern Pharmaceutics 3rd ed., Marcel Dekker, Inc. New York (1996).
NIH: National Cancer Institute, Lymphoma-Patient Version (2015), Web: < http://www.cancer.gov/types/lymphoma>.
Healthline, Non-Hodgkin's Lymphoma (2015), Web: < http://www.healthline.com/health/non-hodgkins-lymphoma#ReadThisNext0>.
Burger et al., "Safety and activity of ibrutinib plus rituximab for patients with high-risk chronic lymphocytic leukaemia: a single-arm, phase 2 study", Lancet Oncology, vol. 15, No. 10, Aug. 2014, pp. 1090-1099.
Damle et al., "Abstract 3531: Changes in immune cell populations in relapsed/refractory CLL patients treated with a Bruton's Tyrosine Kinase (BTK) Inhibitor, Ibrutinib (PCI-32765), in combination with Bendamustine and Rituximab (BR)", Cancer Research, vol. 73, No. 8, Suppl. 1, Apr. 2013, p. 3531
Hoellenriegel et al., "In Vivo Inhibition of BCR Activation in High-Risk CLL Patients on Therapy with Bruton's Tyrosine Kinase Inhibitor Ibrutinib: Correlative Studies from an Ongoing Phase 2 Clinical Trial", Blood, vol. 120, No. 21, 2012, p. 186.
Burger et al., "The Btk Inhibitor Ibrutinib (PCI-32765) in Combination with Rituximab Is Well Tolerated and Displays Profound Activity in High-Risk Chronic Lymphocytic Leukemia (CLL) Patients", Blood, vol. 120, No. 21, 2012, p. 187.
Herter et al., "Preclinical Activity of the Type II CD20 Antibody GA101 (Obinutuzumab) Compared with Rituximab and Ofatumumab In Vitro and in Xenograft Models", Molecular Cancer Therapeutics, vol. 12, No. 10, Oct. 2013, pp. 2031-2042
Golay et al., "Glycoengineered CD20 antibody obinutuzumab activates neutrophils and mediates phagocytosis through CD16B more efficiently than rituximab", Blood, vol. 122, No. 20, Nov. 2013, pp. 3482-3491.
Sehn et al., "Randomized Phase II Trial Comparing GA101 (Obinutuzumab) with Rituximab in Patients with Relapsed CD20 Indolent B-Cell Non-Hodgkin Lymphoma: Preliminary Analysis of the GAUSS Study", Blood, vol. 118, No. 20, 2011, p. 269
International Search Report and Written Opinion dated Jun. 12, 2015 in International Application No. PCT/EP2014/073640.
Stella et al., "Prodrug strategies to overcome poor water solubility," Advanced Drug Delivery Reviews 59 (2007) 677-694.
Extended European Search Report dated Apr. 1, 2015 in European Application No. 12852725.6.
Office Action dated Dec. 17, 2015 in U.S. Appl. No. 14/666,496.
Kozaki et al., "Kinome Reprogramming in DLBCL by the BTK-Specific Inhibitor ONO-4059 Highlights Synergistic Combinations for Clinical Application", haematologica, Jun. 2014, vol. 99, No. Suppl. 1, pp. 137-138.
Lannutti et al., "CAL-101, A Specific Inhibitor of the P110Delta Isoform of Phosphatidylinositide 3-Kinase, for the Treatment of Non-Hodgkins Lymphomas", haematologica, Jun. 2009, vol. 94, No. Suppl. 2, pp. 272-273.
Yang, "Idelalisib: First-in-Class PI3K Delta Inhibitor for the Treatment of Chronic Lymphocytic Leukemia, Small Lymphocytic Leukemia, and Follicular Lymphoma", Clinical Cancer Research, vol. 21, No. 7, Apr. 2015, pp. 1537-1542.
Tannheimer, "Combination of Idelalisib and ONO/GS-4059 in Lymphoma Cell Lines Sensitive and Resistant to BTK Inhibitors", Blood Journal, vol. 126, issue 23, Dec. 2015, p. 3697.
International Search Report dated Jan. 11, 2016 in International (PCT) Application No. PCT/US2016/038763.
International Search Report dated Feb. 24, 2017 in International (PCT) Application No. PCT/US2016/054780.
International Search Report dated Mar. 20, 2017 in International (PCT) Application No. PCT/US2016/054731.
Office Action dated Aug. 11, 2017 in Korean Application No. 10-2016-7014779, with English Translation.
Written Opinion dated Apr. 4, 2017 in Singapore Application No. 11201603613Y.
Byrd et al., "The Btk Inhibitor Ibrutinib (PCI-32765) Alone and in Combination with Rituximab for CLL or SLL", 5 Minute Journal Club (POST-ASH) Issue 2 (2013), 15 pages.
International Search Report dated Jul. 5, 2016 in International Application No. PCT/JP2016/061595.
Waghmare et al., "Propylphosphonic Anhydride (T3P®): An Expedient Reagent for Organic Synthesis", Review Journal of Chemistry, vol. 4, No. 2, 2014, pp. 53-131.

\* cited by examiner

PROPHYLACTIC AGENT AND/OR THERAPEUTIC AGENT FOR DIFFUSE LARGE B-CELL LYMPHOMA

This application claims the priority benefit of Japanese Patent Application No. 2014-061413, filed Mar. 25, 2014, the content of which is incorporated herein in its entirety by reference.

FIELD OF THE INVENTION

The present invention relates to a prophylactic agent and/or a therapeutic agent for activated B cell-like diffuse large B-cell lymphoma, containing compounds represented by general formula (I):

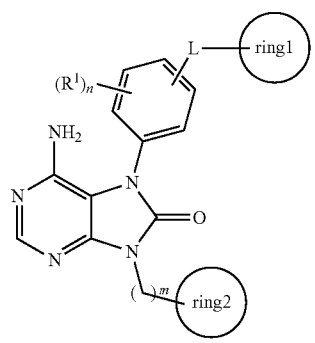

(all of the symbols in the formula have the same definitions as given below), salts thereof, solvates thereof, N-oxides thereof, and prodrugs thereof (hereinafter, may be abbreviated as present compound).

BACKGROUND OF THE INVENTION

Bruton's tyrosine kinase (hereinafter, abbreviated as "Btk") belongs to the Tec family of kinases, which are non-receptor tyrosine kinases, and is selectively expressed in the B cell and myelocyte lines. Btk plays an important role in signal transduction in B cells and is a factor that contributes to the survival, differentiation, proliferation, and activation of B cells. Signaling in B cells via the B cell antigen receptor (BCR) induces a broad range of biological responses, and abnormal signal transduction here causes abnormal B cell activation and the formation of pathogenic autoantibodies. Btk is believed to form a link in the BCR-mediated signal transduction pathways into B cells. In recent years, clinical tests of a Btk inhibitor directed to a variety of B-cell non-Hodgkin's lymphomas have been conducted, and for example, it has been reported that Ibrutinib shows effectiveness in patients with diffuse large B-cell lymphoma (hereinafter, may be abbreviated as DLBCL) (see 54th American society of hematology (ASH), session: 623, program No.: 686, "The Bruton's Tyrosine Kinase (BTK) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase 2 Study", abstract, 2012).

DLBCL is roughly classified into two kinds of activated B-cell like (ABC) and germinal center B-cell like (GCB) depending on a difference in the gene expression profile thereof, and it is known that the former (hereinafter, may be abbreviated as ABC-DLBCL) is of poor prognosis as compared with the latter (hereinafter, may be abbreviated as GCB-DLBCL) (see Nature, Vol. 403, pages 503-511, 2000). Even when treatment is conducted which uses standard treatment methods of B-cell lymphoma, such as radiation, anticancer agents, biological preparations such as Rituxan, or hematopoietic stem cell transplantation, particularly patients with ABC-DLBCL show treatment resistance (refractory) or may repeatedly show recurrence, and therefore, a drug which can attain complete remission of ABC-DLBCL has been desired.

Further, in ABC-DLBCL, mutation is also seen in genes related to NFκ B-cell signaling pathway, such as CD79B and MYD88. CD79B is a membrane protein which forms a protein complex of a B-cell receptor together with CD79A and antigen-specific immunoglobulin. It is known that when there is CD79B mutation, NFκB signaling is constantly activated; however, among ABC-DLBCL patients, frequency thereof is merely about 20 to 30%. Therefore, an agent which can show effectiveness on ABC-DLBCL treatment irrespective of the presence or absence of CD79B mutation has been also desired.

On the other hand, it has been reported that ONO-4059 being the same Btk inhibitor is subjected to a clinical trial in a variety of subtypes of B-cell non-Hodgkin's lymphomas including mantle cell lymphoma and ABC-DLBCL (see 55th American society of hematology (ASH), session: 624, program No.: 4397, "A Phase I Study Of The Oral Btk Inhibitor ONO-4059 In Patients With Relapsed/Refractory B-Cell Lymphoma", abstract, 2013, American Society of Clinical Oncology (ASCO), annual meeting 2014, program No.: 8553, "The Bruton's Tyrosine Kinase (BTK) Inhibitor ONO-4059: Promising Single Agent Activity in Patients with Relapsed and Refractory Non-GCB-DLBCL", abstract). It has been disclosed that the present compound is effective in DLBCL treatment (see WO 2011/152351 and WO 2013/081016), but both the prior art documents do not describe or suggest that the present compound shows prominent effect on which subtype of B-cell non-Hodgkin's lymphoma as compared with other agents.

SUMMARY OF THE INVENTION

An object of the present invention is to provide a medicament which shows more remarkable effect in treatment of activated B-cell like diffuse large B-cell lymphoma (ABC-CLBCL) than the existing Btk inhibitor, and is excellent in safety. Another object of the invention is to provide a medicament which exerts effect, irrespective of the presence or absence of CD79B mutation, which is recognized in a patient with ABC-DLBCL.

That is, the present invention relates to:
[1] a prophylactic agent and/or a therapeutic agent for activated B cell-like diffuse large B-cell lymphoma, comprising 6-amino-9-[(3R)-1-(2-butynoyl)-3-pyrrolidinyl]-7-

(4-phenoxyphenyl)-7,9-dihydro-8H-purin-8-one, a salt thereof, a solvate thereof, an N-oxide thereof, or a prodrug thereof,

[2] the agent according to [1], wherein the activated B-cell like diffuse large B-cell lymphoma is recurrent or refractory activated B-cell like diffuse large B-cell lymphoma,

[3] the agent according to [1] or [2], wherein the activated B-cell like diffuse large B-cell lymphoma is CD79B wild-type activated B-cell like diffuse large B-cell lymphoma,

[4] the agent according to any one of [1] to [3], wherein 6-amino-9-[(3R)-1-(2-butynoyl)-3-pyrrolidinyl]-7-(4-phenoxyphenyl)-7,9-dihydro-8H-purin-8-one, a salt thereof, a solvate thereof, an N-oxide thereof, or a prodrug thereof is orally administered at a dose of 20 to 600 mg per day,

[5] the agent according to any one of [1] to [4], which is a recurrence preventing agent,

[6] the agent according to any one of [1] to [5], which is combined with one or more methods selected from the group consisting of drug therapy using an anticancer agent, a hematopoietic stem cell transplantation method, and radiation therapy,

[7] the agent according to [6], wherein the anticancer agent is an alkylating drug, an antimetabolite, an anticancer antibiotic, a plant alkaloid drug, a hormone drug, a platinum compound, an anti-CD20 antibody, a proteasome inhibitor, a PKC beta inhibitor, an IKK inhibitor, a PI3K inhibitor, a Bcl-2 inhibitor, an mTOR inhibitor, an Aurora kinase inhibitor, a Syk inhibitor, an HDAC inhibitor, a CDK inhibitor, a JAK2 inhibitor, a MEK inhibitor, an HIF-1α inhibitor, a B-RAF-inhibitor, a PDK1 inhibitor, a PLK inhibitor, an NAE inhibitor, a PIM inhibitor, an AXL inhibitor, an EZH2 inhibitor, an HSP inhibitor, a BRD4 inhibitor, an ALK inhibitor, an ABL inhibitor, or the other anticancer agents

[8] the agent according to any one of [1] to [7], which is 6-amino-9-[(3R)-1-(2-butynoyl)-3-pyrrolidinyl]-7-(4-phenoxyphenyl)-7,9-dihydro-8H-purin-8-one hydrochloride,

[9] a method of preventing and/or treating activated B cell-like diffuse large B-cell lymphoma, comprising administering to a human in need thereof a pharmaceutically effective amount of 6-amino-9-[(3R)-1-(2-butynoyl)-3-pyrrolidinyl]-7-(4-phenoxyphenyl)-7,9-dihydro-8H-purin-8-one, a salt thereof, a solvate thereof, an N-oxide thereof, or a prodrug thereof,

[10] 6-amino-9-[(3R)-1-(2-butynoyl)-3-pyrrolidinyl]-7-(4-phenoxyphenyl)-7,9-dihydro-8H-purin-8-one, a salt thereof, a solvate thereof, an N-oxide thereof, or a prodrug thereof, for use in preventing and/or treating activated B cell-like diffuse large B-cell lymphoma in a human, and

[11] a use of 6-amino-9-[(3R)-1-(2-butynoyl)-3-pyrrolidinyl]-7-(4-phenoxyphenyl)-7,9-dihydro-8H-purin-8-one, a salt thereof, a solvate thereof, an N-oxide thereof, or a prodrug thereof, in the preparation of medicament for preventing and/or treating activated B cell-like diffuse large B-cell lymphoma in a human.

The present invention can provide a medicament which shows remarkable effect in treatment of activated B-cell like diffuse large B-cell lymphoma (ABC-DLBCL), inter alia, in treatment of ABC-DLBCL which is developed in a patient having CD79B wild-type gene background, and is excellent in safety.

DETAILED DESCRIPTION OF PREFERRED EMBODIMENTS

The present invention will be described in detail below.
In the present invention, the present invention includes a compound represented by general formula (I):

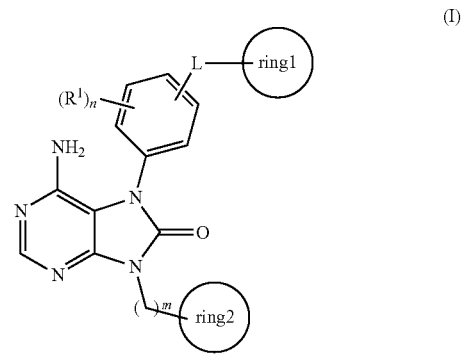

(wherein
L represents (1) —O—, (2) —S—, (3) —SO—, (4) —SO$_2$—, (5) —NH—, (6) —C(O)—, (7) —CH$_2$—O—, (8) —O—CH$_2$—, (9) —CH$_2$—, or (10) —CH(OH)—;
R$^1$ represents (1) a halogen atom, (2) a C$_1$-C$_4$ alkyl group, (3) a C$_1$-C$_4$ alkoxy group, (4) a C$_1$-C$_4$ haloalkyl group, or (5) a C$_1$-C$_4$ haloalkoxy group;
ring 1 represents a 4- to 7-membered cyclic group, which may be substituted with from one to five substituents each independently selected from the group consisting of (1) halogen atoms, (2) C$_1$-C$_4$ alkyl groups, (3) C$_1$-C$_4$ alkoxy groups, (4) nitrile, (5) C$_1$-C$_4$ haloalkyl groups, and (6) C$_1$-C$_4$ haloalkoxy groups, wherein when two or more substituents are present on ring 1, these substituents may form a 4- to 7-membered cyclic group together with the atoms in ring 1 to which these substituents are bound; ring 2 represents a 4- to 7-membered saturated heterocycle, which may be substituted with from one to three —K—R$^2$;
K represents (1) a bond, (2) a C$_1$-C$_4$ alkylene, (3) —C(O)—, (4) —C(O)—CH$_2$—, (5) —CH$_2$—C(O)—, (6) —C(O)O—, or (7) —SO$_2$— (wherein the bond on the left is bound to the ring 2);
R$^2$ represents (1) a C$_1$-C$_4$ alkyl, (2) a C$_2$-C$_4$ alkenyl, or (3) a C$_2$-C$_4$ alkynyl group, each of which may be substituted with from one to five substituents each independently selected from the group consisting of (1) NR$^3$R$^4$, (2) halogen atoms, (3) CONR$^5$R$^6$, (4) CO$_2$R$^7$, and (5) OR$^8$;
R$^3$ and R$^4$ each independently represent (1) a hydrogen atom, or (2) a C$_1$-C$_4$ alkyl group which may be substituted with OR$^9$ or CONR$^{10}$R$^{11}$;
R$^3$ and R$^4$ may, together with the nitrogen atom to which they are bound, form a 4- to 7-membered nitrogenous saturated heterocycle, which may be substituted with an oxo group or a hydroxyl group;
R$^5$ and R$^6$ each independently represent (1) a hydrogen atom, (2) a C$_1$-C$_4$ alkyl group, or (3) a phenyl group;
R$^7$ represents (1) a hydrogen atom or (2) a C$_1$-C$_4$ alkyl group;
R$^8$ represents (1) a hydrogen atom, (2) a C$_1$-C$_4$ alkyl group, (3) a phenyl group, or (4) a benzotriazolyl group;
R$^9$ represents (1) a hydrogen atom or (2) a C$_1$-C$_4$ alkyl group;
R$^{10}$ and R$^{11}$ each independently represent (1) a hydrogen atom or (2) a C$_1$-C$_4$ alkyl group;

n represents an integer from 0 to 4;
m represents an integer from 0 to 2; and
when n is two or more, the $R^1$'s may be the same as each other or may differ from each other), a salt thereof, a solvate thereof, an N-oxide thereof, or a prodrug thereof described in WO 2011/152351, and 6-amino-9-[(3R)-1-(2-butynoyl)-3-pyrrolidynyl]-7-(4-phenoxyphenyl)-7,9-dihydro-8H-purin-8-one hydrochloride described in WO 2013/081016.

In the present invention, the halogen atom denotes fluorine, chlorine, bromine, and iodine.

In the present invention, the C1-4 alkyl group denotes straight-chain and branched-chain C1-4 alkyl groups, e.g., methyl, ethyl, propyl, isopropyl, butyl, sec-butyl, and tert-butyl.

In the present invention, the C1-4 alkylene group denotes methylene, ethylene, propylene, butylene, and their isomers.

In the present invention, the C1-4 alkoxy group denotes straight-chain and branched-chain C1-4 alkoxy groups, e.g., methoxy, ethoxy, propoxy, isopropoxy, butoxy, isobutyloxy, and tert-butoxy.

In the present invention, the C2-4 alkenyl group denotes straight-chain and branched-chain C2-4 alkenyl groups, e.g., ethenyl, 1-propenyl, 2-propenyl, 1-butenyl, 2-butenyl, 3-butenyl, and 1,3-butadienyl.

In the present invention, the C2-4 alkynyl group denotes straight-chain and branched-chain C2-4 alkynyl groups, e.g., ethynyl, 1-propynyl, 2-propynyl, 1-butynyl, 2-butynyl, 3-butynyl, and 1,3-butadiynyl.

In the present invention, the C1-4 haloalkyl group denotes a group provided by substituting one or two or more halogen atoms into a C1-4 alkyl group, and can be exemplified by a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, and a 4-bromobutyl group.

In the present invention, the C1-4 haloalkoxy group denotes a group provided by substituting one or two or more halogen atoms into a C1-4 alkoxy group, and can be exemplified by a trifluoromethoxy group, a trichloromethoxy group, a chloromethoxy group, a bromomethoxy group, a fluoromethoxy group, an iodomethoxy group, a difluoromethoxy group, a dibromomethoxy group, a 2-chloroethoxy group, a 2,2,2-trifluoroethoxy group, a 2,2,2-trichloroethoxy group, a 3-bromopropoxy group, a 3-chloropropoxy group, a 2,3-dichloropropoxy group, a 1-fluorobutoxy group, a 4-fluorobutoxy group, and a 1-chlorobutoxy group.

In the present invention, the 4- to 7-membered cyclic group denotes a C4-7 carbocyclic ring or a 4- to 7-membered heterocycle.

In the present invention, the C4-7 carbocyclic ring denotes a C4-7 monocyclic aliphatic or aromatic carbocyclic ring. The aliphatic system may be partially or completely saturated. Examples here are cyclobutane, cyclopentane, cyclohexane, cycloheptane, cyclopentene, cyclohexene, cycloheptene, cyclobutadiene, cyclopentadiene, cyclohexadiene, cycloheptadiene, and benzene.

In the present invention, the 4- to 7-membered heterocycle denotes a 4- to 7-membered unsaturated heterocycle or a 4- to 7-membered saturated heterocycle.

In the present invention, the 4- to 7-membered unsaturated heterocycle denotes an unsaturated 4- to 7-membered monocyclic heterocycle that contains from one to five hetero atoms selected from the oxygen atom, nitrogen atom, and sulfur atom, and can be exemplified by pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, and thiadiazepine.

In the present invention, the 4- to 7-membered saturated heterocycle denotes a partially or completely saturated 4- to 7-membered monocyclic heterocycle that contains from one to five hetero atoms each independently selected from the oxygen atom, nitrogen atom, and sulfur atom, and can be exemplified by azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetane, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, and dithiane.

In the present invention, the 4- to 7-membered nitrogenous saturated heterocycle refers to those 4- to 7-membered saturated heterocycles that necessarily contain at least one nitrogen atom. Examples are azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, and thiomorpholine.

In the present invention, examples of the salt of the compound represented by general formula (1) include salts with alkali metals (potassium, sodium and the like), salts with alkaline-earth metals (calcium, magnesium and the like), ammonium salt, salts with pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like), and acid addition salts (inorganic acid salts (hydrochloride, hydrobromide, hydroiodide, sulfate, phosphate, nitrate and the like) and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate and the like)).

In the present invention, examples of the solvate of the compound represented by general formula (I) include solvates with water or alcohol solvents (e.g., ethanol).

In the present invention, the N-oxide body of the compound represented by general formula (I) represents a compound represented by general formula (I) in which a nitrogen atom is oxidized. Alternatively, the N-oxide body of the compound represented by general formula (I) may be the alkali (alkaline-earth) metal salts, the ammonium salt, the organic amine salts or the acid addition salts.

In the present invention, the prodrug of the compound represented by general formula (I) refers to a compound which is converted by a reaction in vivo, e.g., by an enzyme or gastric acid, into the compound represented by general formula (I). Examples of the prodrug of the compound represented by general formula (I) include compounds in which, when the compound represented by general formula (I) has a hydroxyl group, this hydroxyl group is acylated, alkylated, phosphated, or borated (e.g., compounds obtained by acetylation, palmitoylation, propanoylation, pivaloylation, succinylation, fumarylation, alanylation, or dimethylaminomethylcarbonylation of the hydroxyl group in the present compound); compounds obtained by esterification or amidation of a carboxyl group in the compound represented by general formula (I) (e.g., compounds obtained by ethyl esterification, isopropyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of a carboxyl group in the compound represented by general formula (I)). These compounds can be prepared by known methods. In addition, the prodrug of the compound represented by general formula (I) may be a hydrate or anhydrous.

Provided herein is method of preventing and/or treating diffuse large B-cell lymphoma (DLBCL) in a human, the method comprising administering to a human in need thereof a pharmaceutically effective amount of a compound of general formula (I), or a salt thereof, a solvate thereof, an N-oxide thereof, or a prodrug thereof.

Also provided is method of preventing and/or treating diffuse large B-cell lymphoma (DLBCL) in a human, the method comprising administering to a human in need thereof a pharmaceutically effective amount of a compound of the formula:

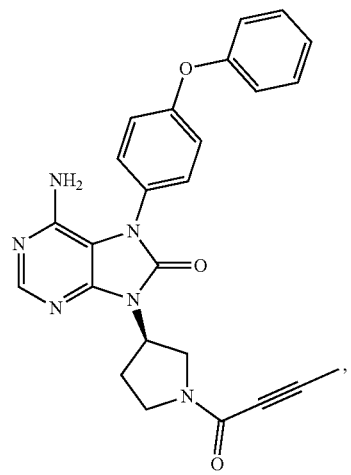 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof.

Provided herein is method of preventing and/or treating activated B-cell like diffuse large B-cell lymphoma (ABC-CLBCL) in a human, the method comprising administering to a human in need thereof a pharmaceutically effective amount of a compound of general formula (I), or a salt thereof, a solvate thereof, an N-oxide thereof, or a prodrug thereof.

Also provided is method of preventing and/or treating activated B-cell like diffuse large B-cell lymphoma (ABC-CLBCL) in a human, the method comprising administering to a human in need thereof a pharmaceutically effective amount of a compound of the formula:

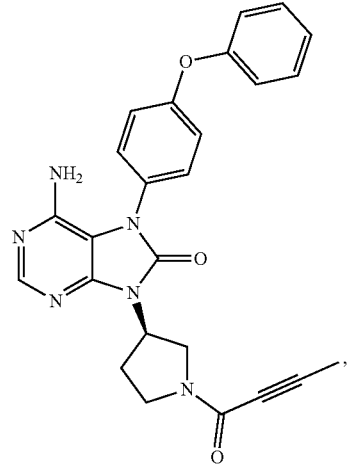 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof.

Provided herein is method of preventing and/or treating a CD79B wild-type activated B-cell like diffuse large B-cell lymphoma in a human, the method comprising administering to a human in need thereof a pharmaceutically effective amount of a compound of general formula (I), or a salt thereof, a solvate thereof, an N-oxide thereof, or a prodrug thereof.

Also provided is method of preventing and/or treating a CD79B wild-type activated B-cell like diffuse large B-cell lymphoma in a human, the method comprising administering to a human in need thereof a pharmaceutically effective amount of a compound of the formula:

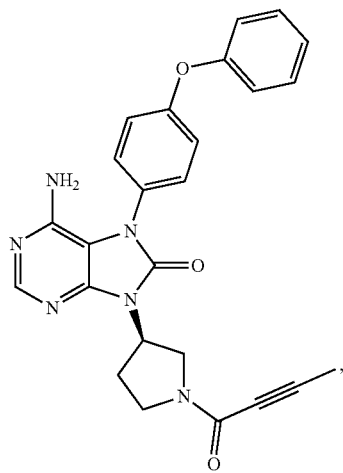 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof.

The terms "pharmaceutically effective amount" and "therapeutically effective amount" refer to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts. A pharmaceutically effective amount includes amounts of an agent which are effective when combined with other agents. Examples of pharmaceutically effective amounts for a compound of general formula (I), including the compound of 6-amino-9-[(3R)-1-(2-butynoyl)-3-pyrrolidinyl]-7-(4-phenoxyphenyl)-7,9-dihydro-8H-purin-8-one hydrochloride, include ranges of from about 20 mg to about 600 mg per day, specifically including separate amounts of about 20 mg, about 40 mg, about 50 mg, about 80 mg, about 100 mg, about 160 mg, about 200 mg, about 250 mg, about 300 mg, about 320 mg, about 400 mg, about 480 mg, about 500 mg, about 570 mg, and about 600 mg per day in a single dose or in divided doses, such as twice per day, three times per day, and four times per day.

Provided is a compound of general formula (I), or a salt thereof a solvate thereof, an N-oxide thereof, or a prodrug thereof, for use as a medicament.

Also provided is the use of a compound of the formula:

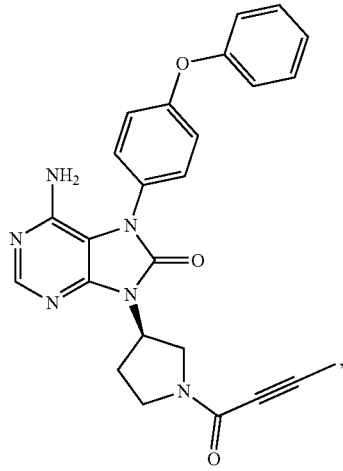 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, for use as a medicament.

Also provided is a hydrochloride salt of the compound of this formula for use as a medicament.

Also provided is a compound of the formula:

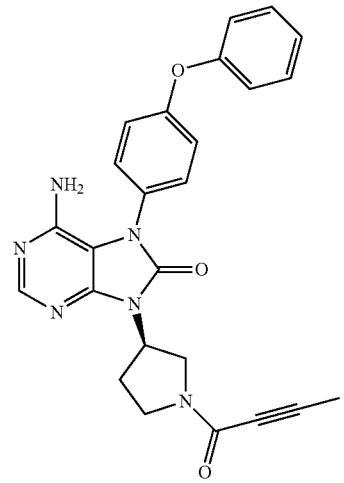

or a salt thereof, a solvate thereof, an N-oxide thereof, or a prodrug thereof, for use as a medicament, wherein the medicament comprises from about 20 mg to about 600 mg of the compound of general formula (I), or a salt thereof, a solvate thereof, an N-oxide thereof, or a prodrug thereof.

Provided is a compound of general formula (I), or a salt thereof, a solvate thereof, an N-oxide thereof, or a prodrug thereof, for use in preventing and/or treating diffuse large B-cell lymphoma (DLBCL) in a human.

Also provided is a compound of the formula:

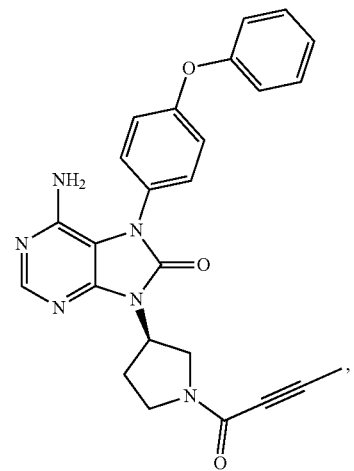 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, for use in preventing and/or treating diffuse large B-cell lymphoma (DLBCL) in a human.

Provided is a compound of general formula (I), or a salt thereof, a solvate thereof, an N-oxide thereof, or a prodrug thereof, for use in preventing and/or treating activated B-cell like diffuse large B-cell lymphoma (ABC-CLBCL) in a human.

Also provided is a compound of the formula:

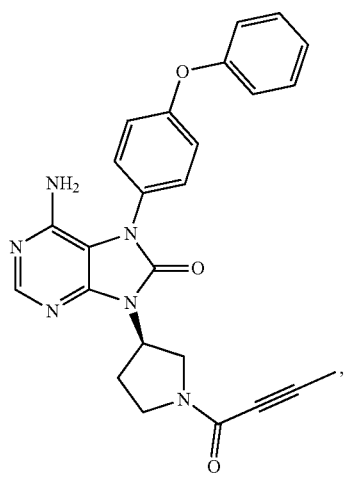

or a salt thereof, a solvate thereof, an N-oxide thereof, or a prodrug thereof, for use in preventing and/or treating activated B-cell like diffuse large B-cell lymphoma (ABC-CLBCL) in a human.

Provided is a compound of general formula (I), or a salt thereof, a solvate thereof, an N-oxide thereof, or a prodrug thereof, for use in preventing and/or treating a CD79B wild-type activated B-cell like diffuse large B-cell lymphoma in a human.

Also provided is a compound of the formula:

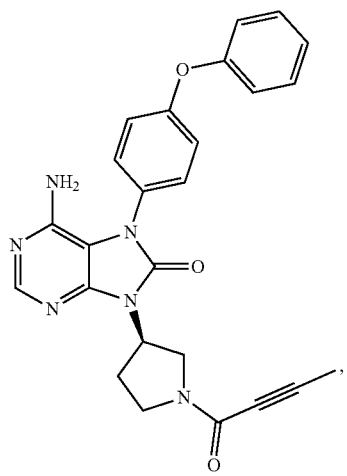 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, for use in treating a CD79B wild-type activated B-cell like diffuse large B-cell lymphoma in a human.

Provided is the use of a compound of general formula (I), or a salt thereof, a solvate thereof, an N-oxide thereof, or a prodrug thereof, in the preparation of a medicament for preventing and/or treating diffuse large B-cell lymphoma in a human.

Also provided is the use of a compound of the formula:

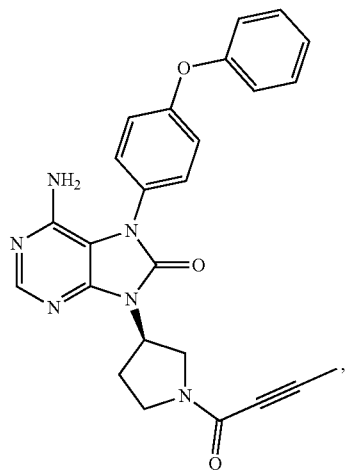 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, in the preparation of a medicament for preventing and/or treating diffuse large B-cell lymphoma in a human.

Also provided is the use of a compound of general formula (I), or a salt thereof, a solvate thereof, an N-oxide thereof, or a prodrug thereof, in the preparation of a medicament for preventing and/or treating activated B-cell like diffuse large B-cell lymphoma (ABC-CLBCL) in a human.

Further provided is the use of a compound of general formula (I), or a salt thereof, a solvate thereof, an N-oxide thereof, or a prodrug thereof, in the preparation of a medicament for preventing and/or treating activated B-cell like diffuse large B-cell lymphoma (ABC-CLBCL) in a human, wherein the medicament comprises from about 20 mg to about 600 mg of the compound of general formula (I), or a salt thereof, a solvate thereof, an N-oxide thereof, or a prodrug thereof.

Also provided is the use of a compound of the formula:

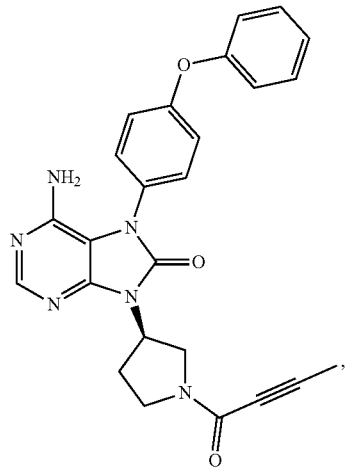 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, in the preparation of a medicament for preventing and/or treating activated B-cell like diffuse large B-cell lymphoma (ABC-CLBCL) in a human.

Further provided is the use of a compound of the formula:

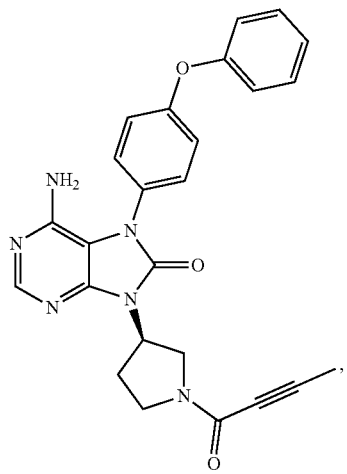

or a salt thereof, a solvate thereof, an N-oxide thereof, or a prodrug thereof, in the preparation of a medicament for preventing and/or treating activated B-cell like diffuse large B-cell lymphoma (ABC-CLBCL) in a human, wherein the medicament comprises from about 20 mg to about 600 mg of the compound of general formula (I), or a salt thereof, a solvate thereof, an N-oxide thereof, or a prodrug thereof.

A further embodiment provides the use of 6-amino-9-[(3R)-1-(2-butynoyl)-3-pyrrolidinyl]-7-(4-phenoxyphenyl)-7,9-dihydro-8H-purin-8-one hydrochloride in the preparation of a medicament for preventing and/or treating activated B-cell like diffuse large B-cell lymphoma (ABC-CLBCL) in a human.

Another embodiment provides the use of a hydrochloride salt of a compound of the formula:

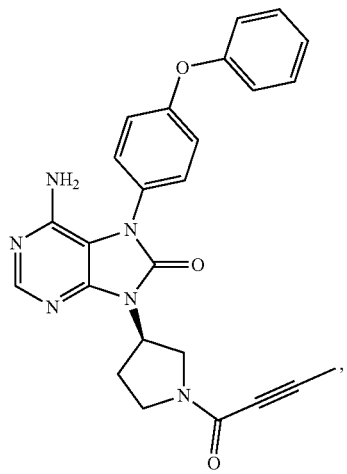

or a salt thereof, a solvate thereof, an N-oxide thereof, or a prodrug thereof, in the preparation of a medicament for preventing and/or treating activated B-cell like diffuse large B-cell lymphoma (ABC-CLBCL) in a human, wherein the medicament comprises from about 20 mg to about 600 mg of the compound, or a salt thereof, a solvate thereof, an N-oxide thereof, or a prodrug thereof.

Also provided is the use of a compound of general formula (I), or a salt thereof, a solvate thereof, an N-oxide thereof, or a prodrug thereof, in the preparation of a medicament for preventing and/or treating a CD79B wild-type activated B-cell like diffuse large B-cell lymphoma in a human.

Additionally provided is the use of a compound of general formula (I), or a salt thereof, a solvate thereof, an N-oxide thereof, or a prodrug thereof, in the preparation of a medicament for preventing and/or treating a CD79B wild-type activated B-cell like diffuse large B-cell lymphoma in a human, wherein the medicament comprises from about 20 mg to about 600 mg of the compound of general formula (I), or a salt thereof, a solvate thereof, an N-oxide thereof, or a prodrug thereof.

Also provided is the use of a compound of the formula:

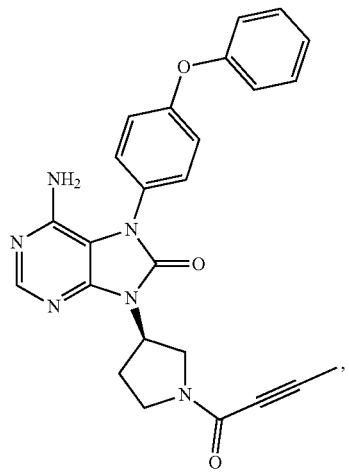 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, in the preparation of a medicament for preventing and/or treating a CD79B wild-type activated B-cell like diffuse large B-cell lymphoma in a human.

Further provided is the use of a compound of the formula:

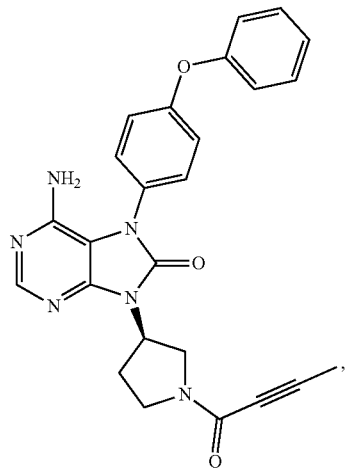 [SMILES: CC#CC(=O)N1CC[C@@H](n2c(=O)n(-c3ccc(Oc4ccccc4)cc3)c3c(N)ncnc32)C1]

or a salt thereof, a solvate thereof, an N-oxide thereof, or a prodrug thereof, in the preparation of a medicament for preventing and/or treating a CD79B wild-type activated B-cell like diffuse large B-cell lymphoma in a human, wherein the medicament comprises from about 20 mg to about 600 mg of the compound of the compound, or a salt thereof, a solvate thereof, an N-oxide thereof, or a prodrug thereof.

A further embodiment provides the use of a hydrochloride salt of a compound of the formula:

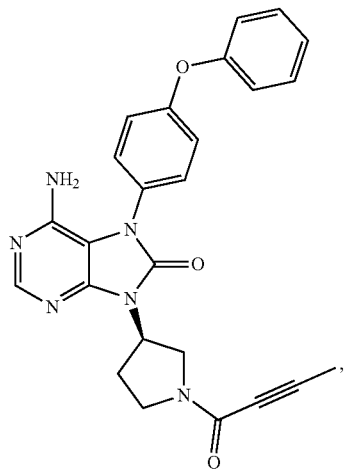 [SMILES: CC#CC(=O)N1CC[C@@H](n2c(=O)n(-c3ccc(Oc4ccccc4)cc3)c3c(N)ncnc32)C1]

in the preparation of a medicament for preventing and/or treating a CD79B wild-type activated B-cell like diffuse large B-cell lymphoma in a human.

In the present invention, the term "preventing" (or "prevent" or "prevention") refers to the inhibition of, or the decrease in the occurrence or severity of, a symptom, disorder, condition, or disease or the decrease in the risk of acquiring a symptom, disorder, condition, or disease or its associate symptoms.

In the present invention, malignant lymphoma includes non-Hodgkin's lymphomas (NHL), among which B-cell non-Hodgkin's lymphomas are particularly suitable. Examples thereof include Burkitt's lymphoma, AIDS-related lymphoma, marginal zone B-cell lymphoma (nodal marginal zone B-cell lymphoma, extranodal marginal zone B-cell lymphoma, and splenic marginal zone B-cell lymphoma), diffuse large B-cell lymphoma, primary effusion lymphoma, lymphomatoid granulomatosis, follicular lymphoma, B-cell chronic lymphocytic leukemia, B-cell prolymphocytic leukemia, lymphoplasmacytic leukemia/Waldenstrom's macroglobulinemia, plasmacytoma, mantle cell lymphoma, mediastinal large B-cell lymphoma, intravascular large B-cell lymphoma, and hairy cell leukemia.

In the present invention, examples of the diffuse large B-cell lymphoma include activated B-cell like diffuse large B-cell lymphoma and germinal center B-cell like diffuse large B-cell lymphoma, and activated B-cell like diffuse large B-cell lymphoma is preferable.

In the present invention, the activated B-cell like diffuse large B-cell lymphoma includes recurrent and refractory activated B-cell like diffuse large B-cell lymphomas.

In the present invention, the recurrent activated B-cell like diffuse large B-cell lymphoma means a patient who attained Complete Response (CR), Complete Response, unconfirmed (CRu), CR with incomplete marrow recovery (CRi) or Partial Response (PR) for 6 months or longer after the last treatment of activated B-cell like diffuse large B-cell lymphoma, and for whom pathological advance was recognized, as is defined in Examples later.

In the present invention, the refractory activated B-cell like diffuse large B-cell lymphoma means a patient who could not attain CR, CRu, Cri or PR after the last treatment of activated B-cell like diffuse large B-cell lymphoma, or a patient who acquired CR, CRu, CRi or PR for shorter than 6 months after the last treatment, but for whom pathological advance was recognized, as is defined in Examples later.

In the present invention, the activated B-cell like diffuse large B-cell lymphoma includes activated B-cell like diffuse large B-cell lymphoma which has been developed in a patient having CD79B wild-type or mutant gene background.

In the present invention, the CD79B wild-type activated B-cell like diffuse large B-cell lymphoma means activated B-cell like diffuse large B-cell lymphoma which has been developed in a patient having CD79B wild-type gene background.

In the present invention, examples of the dose of the present compound include a range of about 20 mg to about 600 mg per day, specifically, about 20 mg, about 40 mg, about 80 mg, about 160 mg, about 320 mg, about 480 mg, about 570 mg, and about 600 mg per day.

In the present invention, the present compound has showed therapeutic effect on recurrent or refractory activated B-cell like diffuse large B-cell lymphoma which was developed in a patient who had already received standard treatment for NHL, and therefore, it can be also used for preventing recurrence of the disease.

In the present invention, examples of the treatment method which can be used in combination with the present compound include drug therapy using other anticancer agents, a hematopoietic stem cell transplantation method, and radiation therapy.

In the present invention, examples of the other anticancer agents used in the drug therapy include an alkylating drug, an antimetabolite, an anticancer antibiotic, a plant alkaloid drug, a hormone drug, a platinum compound, an anti-CD20 antibody, a proteasome inhibitor, a protein kinase C (PKC) beta inhibitor, an IκB kinase (IKK) inhibitor, a phosphoinositide 3-kinase (PI3K) inhibitor, a B-cell lymphoma 2 (Bcl-2) inhibitor, a mammalian target of rapamycin (mTOR) inhibitor, an Aurora kinase inhibitor, a spleen tyrosine kinase (Syk) inhibitor, a histon deacetylase (HDAC) inhibitor, a cyclin-dependent kinase (CDK) inhibitor, a Janus kinase 2 (JAK 2) inhibitor, a mitogen-activated protein kinase (MEK) inhibitor, a hypoxia inducible factor-1α (HIF-1α) inhibitor, a proto oncogene B-Raf (B-RAF) inhibitor, a 3-phosphoinositied-dependent kinase 1 (PDK1) inhibitor, a polo-like kinase 1 (PLK) inhibitor, an nedd8-activating enzyme (NEA) inhibitor, a proto-oncogene protein pim-1 (PIM) inhibitor, an Axl receptor tyrosine kinase (AXL) inhibitor, an enhancer of zeste homolog 2 (EZH2) inhibitor, heat-shock protein (HSP) inhibitor, bromodomain containing 4 (BRD4) inhibitor, anaplastic lymphoma kinase (ALK) kinase, proto-oncogene abl (ABL) inhibitor and the like.

Examples of the alkylating drug include nitrogen mustard-N-oxide hydrochloride, cyclophosphamide, chlorambucil, ifosfamide, melphalan, thiotepa, carboquone, busulfan, nimustine hydrochloride, dacarbazine, ranimustine, carmustine, streptozotocin, triethylene melamine, mitomycin C and the like.

Examples of the antimetabolite include methotrexate, mercaptopurine, 6-mercaptopurine riboside, 6-thioguanine, 5-fluorouracil, capecitabine, decarbazine, tegafur, tegafur uracil, carmofur, doxifluridine, cytarabine, enocitabine, tegafur gimestat otastat potassium, gemcitabine hydrochloride, cytarabine ocfosfate, procarbazine hydrochloride, hydroxycarbamide and the like.

Examples of the anticancer antibiotic include actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer, mithramycin and the like.

Examples of the plant alkaloid drug include vinblastine sulfate, vincristine sulfate, vindesine sulfate, irinotecan hydrochloride, etoposide, flutamide, vinorelbine tartrate, docetaxel hydrate, paclitaxel and the like.

Examples of the hormone drug include estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, exemestane and the like.

Examples of the platinum compound include carboplatin, cisplatin, nedaplatin and the like.

Examples of the anti-CD20 antibody include rituximab, ibritumomab, ocrelizumab, ofatumumab, tositumomab and the like.

Examples of the proteasome inhibitor include bortezomib, carfilzomib, NPI-0052 and the like.

Examples of the PKC beta inhibitor include enzastaurin, sotrastaurin, BHA536, LY33351 and the like.

Examples of the IKK inhibitor include AFN700, MLN120B and the like.

Examples of the PI3K inhibitor include CAL-101, IPI-145, PI103 and the like.

Examples of the Bcl-2 inhibitor include navitoclax (ABT-263), ABT-737, ABT-199, AT-101, obatoclax and the like.

Examples of the mTOR inhibitor include everolimus, rapamycin (sirolimus), temsirolimus and the like.

Examples of the Aurora kinase inhibitor include alisertib, AT9283, MLN8237, AZD1152 and the like.

Examples of the Syk inhibitor include fostamatinib, R406 and the like.

Examples of the HDAC inhibitor include suberoylanilide hydroxamic acid (SAHA), romidepsin, vorinostat, panobinostat, entinostat, valproic acid, trichostatin A (TSA) and the like.

Examples of the CDK inhibitor include dinaciclib, palbociclib (PD-0332911) and the like.

Examples of the JAK2 inhibitor include fedratinib, ruxolitinib, baricitinib, tasocitinib, SB 1518, AT9283 and the like.

Examples of the MEK inhibitor include trametinib, AZD6244 and the like.

Examples of the HIF-1a inhibitor include PX-478 and the like.

Examples of the B-RAF inhibitor include vemurafenib and the like.

Examples of the PDK-1 inhibitor include BX-192 and the like.

Examples of the PLK inhibitor include BI-6227, GSK-461364 and the like.

Examples of the NAE inhibitor include MLN-4924 and the like.

Examples of the PIM inhibitor include AZD-1208 and the like.

Examples of the AXL inhibitor include BGB-324, ASP2215 and the like.

Examples of the EZH2 inhibitor include GSK-342 and the like.

Examples of the HSP inhibitor include NYP-AUY-922 and the like.

Examples of the BRD4 inhibitor include CPI-203 and the like.

Examples of the ALK inhibitor include crizotinib, alectinib, ceritinib and the like.

Examples of the ABL inhibitor include imatinib, nilotinib, dasatinib, bosutinib and the like.

In the present invention, examples of the other anticancer agents used in the drug therapy include L-asparaginase, octreotide acetate, porfimer sodium, mitoxantrone acetate, folinic acid, lenalidomide and the like.

In the present invention, examples of the other Btk inhibitor include Ibrutinib (PCI-32765), CC-292 (AVL-292), HM-71224, ACP-196, SNS-062 and the like.

In the present invention, the hematopoietic stem cell transplantation method includes autologous hematopoietic stem cell transplantation and allogenic hematopoietic stem cell transplantation. In the present invention, when allogenic hematopoietic stem cell transplantation is conducted, while being obvious to a person skilled in the art, whether or not HLA of a donor donating a stem cell is compatible is determined depending on the type of a human leukocyte antigen (HLA) of a patient.

In the present invention, the hematopoietic stem cell transplantation can be also classified depending on a hematopoietic stem cell to be used, and includes, for example, bone marrow transplantation, peripheral blood stem cell transplantation, and umbilical cord blood transplantation.

In the present invention, the radiation therapy includes external radiation and internal radiation. The external radiation is also called External Beam Radiation Therapy (EBRT). An apparatus to be used in the external radiation is not particularly limited as far as it is used for the treatment of malignant lymphoma, and examples thereof include liniac, linac, microtron and betatron.

In the present invention, the internal radiation is also called Brachytherapy (BH). Specifically, examples thereof include a method of sealing a radioisotope in a container having a shape of tube, needle, wire, particulate or the like, and using the resulting product as a radiation source, a method of administering a radioisotope in the form of a medicament such as a capsule, an injection or the like, or a method of administering a so-called labeled body in which an antibody such as an anti-CD20 antibody used in the treatment of malignant lymphoma is bound with a radioisotope. The radioisotope used herein is not particularly limited as far as it is used in the treatment of malignant lymphoma, and examples thereof include radium, yttrium 90, indium 113, cesium 137, iridium 192, gold 198, iodine 123, iodine 131, and strontium 89.

In the present invention, a treatment method which can be used in combination with the present compound may be applied simultaneously with administration of the present compound, or may be applied at different times. When the treatment method which can be used together is applied at different times, it may be applied before or after administration of the present compound In the present invention, examples of the present compound preferably include compounds described in the working examples of WO 2011/152351 and WO 2013/081016, and more preferably include 9-(1-acryloyl-3-azetidinyl)-6-amino-7-(4-phenoxyphenyl)-7,9-dihydro-8H-purin-8-one, 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, 9-[(1-acryloyl-4-piperidinyl)methyl]-6-amino-7-(4-phenoxyphenyl)-7,9-dihydro-8H-purin-8-one, 6-amino-9-[(3R)-1-(2-butynoyl)-3-pyrrolidinyl]-7-(4- phenoxyphenyl)-7,9-dihydro-8H-purin-8-one, 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, 6-amino-7-[4-(3-chlorophenoxy)phenyl]-9-{(3R)-1-[(2E)-4-(dimethylamino)-2-butenoyl]-3-pyrrolidinyl)}-7,9-dihydro-8H-purin-8-one, 6-amino-9-[1-(2-butynoyl)-3-pyrrolidinyl]-7-(4-phenoxyphenyl)-7,9-dihydro-8H-purin-8-one, 6-amino-9-{1-[(2E)-4-(dimethylamino)-2-butenoyl]-3-pyrrolidinyl}-7-(4-phenoxyphenyl)-7,9-dihydro-8H-purin-8-one, or 6-amino-9-[(3R)-1-(2-butynoyl)-3-pyrrolidinyl]-7-(4-phenoxyphenyl)-7,9-dihydro-8H-purin-8-one hydrochloride. Examples of the present compound particularly preferably include 6-amino-9-[(3R)-1-(2-butynoyl)-3-pyrrolidinyl]-7-(4-phenoxyphenyl)-7,9-dihydro-8H-purin-8-one hydrochloride, and this is a compound represented by the following structural formula.

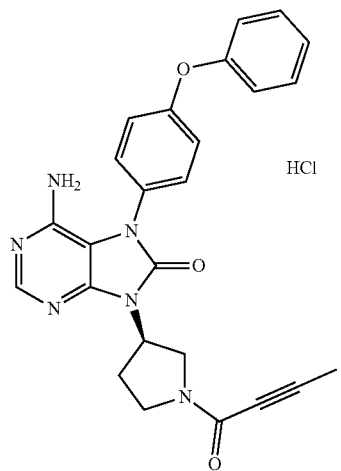 [SMILES: CC#CC(=O)N1CC[C@@H](n2c(=O)n(-c3ccc(Oc4ccccc4)cc3)c3c(N)ncnc32)C1 ; Cl]

[Isomers]

The present compound encompasses all isomers, unless specifically indicated otherwise. For example, alkyl groups include both linear alkyl groups and branched alkyl groups. Moreover, all of the following are included in the present compound: geometric isomers (E configuration, Z configuration, cis configuration, trans configuration) for double bonds, rings, and condensed rings; optical isomers due to, for example, the presence of an asymmetric carbon atom (R and S configurations, α and β positions, enantiomers, diastereomers); optically active forms that exhibit optical rotation (D, L, d, and l configurations); polar forms generated by chromatographic separation (high-polarity forms, low-polarity forms); equilibrium compounds; rotational isomers; mixtures thereof in any proportions; and racemic mixtures. The present compound also encompasses all isomers arising due to tautomers.

Further, an optical isomer in the present compound may include not only 100% pure optical isomers, but also other optical isomers at less than 50%.

In the present invention, unless otherwise indicated, and as is clear to a parson skilled in the art, the symbol ⟋ represents α-position, β-position or a mixture thereof in any proportion.

[Method for Producing Present Compound]

The present compound can be produced by suitably modifying and combining the method described in WO 2011/152351, the method described in WO 2013/081016, known methods, for example, the method described in Comprehensive Organic Transformation: A Guide to Functional Group Preparations, 2nd Edition (Richard C. Larock, John Wiley & Sons Inc., 1999) or the like.

[Toxicity]

The present compound has sufficiently low toxicity, and can be safely used as a medicament.

The present compound is usually administered systemically or locally in an oral or parenteral form. Examples of the oral preparation include liquids for oral administration (e.g., elixirs, syrups, pharmaceutically acceptable water-based preparations, suspensions, and emulsions) and solids for oral administration (e.g., tablets (including sublingual tablets and orally disintegrating tablets), pills, capsules (including hard capsules, soft capsules, gelatin capsules, and microcapsules), powders, granules, and lozenges). Examples of the parenteral preparations include solutions (e.g., injectables (e.g., subcutaneous injectables, intravenous injectables, intramuscular injectables, intraperitoneal injectables, and drip preparations), eye drops (e.g., aqueous eye drops (e.g., aqueous eye drops, aqueous eye drop suspensions, viscous eye drops, and solubilized eye drops) and nonaqueous eye drops (e.g., nonaqueous eye drops and nonaqueous eye drop suspensions)), topicals (e.g., ointments (e.g., ophthalmic ointments)), and ear drops). These preparations may be release-controlled preparations such as rapid-release preparations and sustained-release preparations. These preparations can be produced by known methods, for example, by the methods described in The Japanese Pharmacopoeia.

The liquids for oral administration as oral preparations can be produced, for example, by dissolving, suspending, or emulsifying effective components in a commonly used diluent (e.g., purified water, ethanol, or a mixture thereof). These liquids may also contain, for example, a wetting agent, a suspending agent, an emulsifying agent, a sweetener, a flavor, a fragrance, a preservative, a buffer and the like.

The solids for oral administration as oral preparations is formulated into preparations, for example, by mixing effective components with a vehicle (e.g., lactose, mannitol, glucose, microcrystalline cellulose, and starch), a binder (e.g., hydroxypropyl cellulose, polyvinylpyrrolidone, and magnesium metasilicate aluminate), a disintegrant (e.g., cellulose calcium glycolate), a lubricant (e.g., magnesium stearate), a stabilizer, a dissolution adjuvant (e.g., glutamic acid and aspartic acid) and the like according to standard methods. As necessary, coating may be carried out with a coating agent (e.g., sugar, gelatin, hydroxypropyl cellulose, and hydroxypropyl methyl cellulose phthalate) and two or more layers may be applied.

The topicals as parenteral preparations are produced by a known method or a formulation in common use. For example, an ointment is produced by incorporating or melting effective components into a base. The ointment base is selected from known ointment bases or an ointment base in common use. For example, ointment bases selected from higher fatty acids and higher fatty acid esters (e.g., adipic acid, myristic acid, palmitic acid, stearic acid, oleic acid, adipate esters, myristate esters, palmitate esters, stearate esters, and oleate esters), waxes (e.g., beeswax, whale wax, and ceresin), surfactants (e.g., polyoxyethylene alkyl ether phosphate esters), higher alcohols (e.g., cetanol, stearyl alcohol, and cetostearyl alcohol), silicone oils (e.g., dimethylpolysiloxane), hydrocarbons (e.g., hydrophilic petrolatum, white petrolatum, purified lanolin, and liquid paraffin), glycols (e.g., ethylene glycol, diethylene glycol, propylene glycol, polyethylene glycol, and macrogol), plant oils (e.g., castor oil, olive oil, sesame oil, and turpentine oil), animal oils (e.g., mink oil, egg yolk oil, squalane, and squalene), water, absorption promoters, and anti-irritant are used alone, or are used by mixing two or more kinds thereof. The ointment base may further contain a humectant, a preservative, a stabilizer, an antioxidant, a flavoring agent and the like.

The injectables as parenteral preparations encompass solutions, suspensions, and emulsions as well as solid injectables used by dissolution or suspension in a solvent at the time of use. For example, the injectables are used in which effective components are dissolved, suspended, or emulsified in a solvent. As the solvent, for example, distilled water for injection, physiological saline solution, plant oil, propylene glycol, polyethylene glycol, alcohols such as ethanol, and a combination thereof are used. The injectables may also contain a stabilizer, a dissolution adjuvant (e.g., glutamic acid, aspartic acid, and Polysorbate 80 (registered trade mark)), a suspending agent, an emulsifying agent, a soothing agent, a buffer, a preservative and the like. The injectables are sterilized in the final step or are produced using aseptic processing. The injectables may also be produced as a sterile solid form, for example, a freeze-dried product, and may be used after dissolution in distilled water for injection or another solvent, which is either sterile or sterilized prior to use.

In order to use the present compound, or to use the present compound and the treatment method to be used in combination with the present compound for the above purpose, the present compound is usually administered systemically or locally in an oral or parenteral form (in the case of external radiation, exposure to radiation). The dose is different depending on age, weight, symptom, therapeutic effect, administration method, treating time and the like, and the present compound is usually administered to an adult orally in the range from 1 ng to 1000 mg from one to several times per day, or is parenterally administered to an adult in the range from 0.1 ng to 100 mg from one to several times per day, or is intravenously administered continuously in the range from 1 hour to 24 hours per day. Of course, since the dose varies depending on a variety of conditions as described above, cases may occur in which an amount less than the above dosage levels is sufficient or in which administration is required while exceeding these ranges. When external radiation is applied, a treatment schedule to be conducted for treating malignant lymphoma is usually adopted, and an example of the treatment schedule include a schedule in which fractionated radiation is conducted at a dose level of about 1.8 to 2.0 gray (Gy) per day for a period of about 4 to 5 days in one week during a term of 1 to 6 weeks, in which about 10 to 80 Gy is radiated as a total dose.

EXAMPLES

The present invention will be described in detail below by way of examples, but the invention is not limited thereto.

Example 1: Therapeutic Effect of Present Compound in ABC-DLBCL Patients

A clinical trial was conducted by an open label multicenter non-randomized test by administering 6-amino-9-[(3R)-1-(2-butynoyl)-3-pyrrolidinyl]-7-(4-phenoxyphenyl)-7,9-dihydro-8H-purin-8-one hydrochloride, the present compound, as monotherapy to an ABC-DLBCL patient.

[Subject to be Administered]

Among the patients who had already received treatment, who had been diagnosed as a non-Hodgkin's lymphoma, for whom higher preference order of treatment was not present, and who fell under the following definition of "recurrent" or "refractory", patients satisfying the following conditions entered.

Recurrent: Patients who attained Complete Response (CR), Complete Response, unconfirmed (CRu), CR with incomplete marrow recovery (CRi) or Partial Response (PR) for 6 months or longer after the last treatment of non-Hodgkin's lymphoma, and for whom pathological advance was recognized.

Refractory: Patients who could not attain CR, CRu, CRi or PR after the last treatment of non-Hodgkin's lymphoma, or patients who acquired CR, CRu, CRi or PR for shorter than 6 months after the last treatment, but for whom pathological advance was recognized.

Condition: Two or more NHL treatments have already failed.

[Administration Schedule]

A fixed dose of the present compound was orally administered once per day, with one cycle being treatment for 28 days in 3 patients per one cohort. The schedule was such that this cycle was conducted until 6 cycles, and could be maximally extended to 24 cycles. In the first cohort, all the patients were administered at a fixed dose of 20 mg of the present compound. When there was no toxicity, the dose was gradually increased at an increment not exceeding 100% until toxicity associated with the present compound was observed. An example of the administration schedule is shown in the following table.

TABLE 1

| Cohort | Dose | Gradual increase rate |
| --- | --- | --- |
| 1 | 20 mg | — |
| 2 | 40 mg | 100% |
| 3 | 80 mg | 100% |
| 4 | 160 mg | 100% |
| 5 | 320 mg | 100% |
| 6 | 480 mg | 50% |
| 7 | 570 mg | 20% |

[Determination of Carcinoma]

Regarding the NHL patients who entered under the above conditions, an immunohistochemical method or gene expression profiling was conducted according to a conventional method using a diagnostic sample obtained by tissue biopsy excising a part of affected lymph node, so that patients affected with ABC-DLBCL were extracted.

[Evaluation Items]

Primary evaluation items were safety, tolerance and dose limiting toxicities (DLTs). These items were evaluated using manifestation of adverse event, physical examination, clinical test, vital sign and cardiograph. In addition, the intensity of the adverse event was determined using Common Terminology Criteria for Adverse Events (CTCAE) version 4.0 of the National Cancer Institute.

Secondary evaluation items were Overall Response Rate (ORR), Complete Response Rate (CR, CRu, CRi), Partial Response Rate (PR), Progression Free Survival (PFS), Overall Survival (OS), Duration of Response, Event Free Survival (EFS), Pharmacokinetics (PK) and Pharmacodynamics (PD). In addition, the evaluations of CR, CRu and PR were conducted by referring to evaluation criteria described in Journal of Clinical Oncology, Vol. 17, No. 4, pages 1244-1253, 1999.

[Results]

A decrease in lymph node swelling was recognized in 6 of 8 ABC-DLBCL patients in the first administration cycle of the present compound. Further, the present compound was administered by cohort 4 (160 mg) or cohort 5 (520 mg) of the administration schedule, and as a result, ORR was 75% (6 PR cases (median value of decrease in lymph node was 81.5%) and 2 disease progression cases in 8 cases). In addition, high tolerance was confirmed in 13 ABC-DLBCL patients to whom the present compound had been administered. The adverse event associated with the present compound was confirmed in 5 cases of 13 cases, and among them, 2 cases of the adverse event were events classified into grade 3 according to CACTE (drug reaction and lymphopenia). Further, a bleeding-associated event such as intracranial bleeding was not seen at all as the adverse event.

[Gene Analysis]

Biopsy samples of tumor were obtained from ABC-DLBCL patients before administration of the present compound. From the samples, genomic DNA was extracted by conventional method, and the presence or absence of CD79B mutation was confirmed in accordance with the method described in Nature, No. 463, pages 88-92, 2010. As a result, it was seen that, among the 8 ABC-DLBCL patients, all of 7 evaluable patients had CD79B wild-type gene background.

Comparative Example 1: Therapeutic Effect of Comparative Compound in ABC-DLBCL Patients As a comparative example, the clinical trial result of PCI-32765, (General name: Ibrutinib, hereinafter, referred to as comparative compound) a Btk inhibitor, having the same pharmacological activity as that of the present compound is cited as follows in the present specification from the description of 54$^{th}$ American society of hematology (ASH), session: 623, program No.: 686, "The Bruton's Tyrosine Kinase (BTK) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase 2 Study", abstract, 2012.

[Method]

The comparative compound was orally administered to recurrent or refractory DLBCL patients at a dose of 560 mg once per day. Using an Affymetrix array, the gene expression profiling of a biopsy tissue embedded in paraffin fixed with formalin was conducted to identify a subtype (ABC, GCB, classification impossible) of DLBCL. Using Sanger sequencing, CD79B mutation was identified. A primary evaluation item was ORR, and evaluation of response was conducted using International Working Group Criteria for NHL.

[Results]

Seventy patients were registered, and among them, the number of patients with ABC-DLBCL was 29. The comparative compound was administered to the ABC-DLBCL patients by single dose (560 mg), and as a result, ORR was 40% (10 cases in 25 cases, that is, CR was 8% (2 cases in 25 cases) and PR was 32% (8 cases in 25 cases) as breakdowns of the 10 cases). Four cases in 29 cases were patients for whom response could not be evaluated. Among them, the number of patients for whom the presence or absence of CD79B mutation could be confirmed was 24, and in the patients having CD79B mutation, ORR thereof was 60% (3 cases in 5 cases), and in the patients having CD79B wild-type, ORR thereof was 37% (7 cases in 19 cases).

From the above results, effectiveness on the ABC-DLBCL patients was such that Overall Response Rate (ORR) thereof was 75% in the present compound, while ORR thereof was 40% in the comparative compound. Further, effectiveness on the ABC-DLBCL patients having CD79B wild-type was such that Overall Response Rate (ORR) thereof was 85% (6 cases in 7 cases) in the present compound, while ORR thereof was 37% in the comparative compound.

Therefore, it was seen that the present compound exhibits more remarkable therapeutic effect on ABC-DLBCL patients, inter alia, ABC-DLBCL patients having CD79B wild-type gene background than the comparative compound, although the comparative compound is a compound having the same pharmacological activity (Btk inhibition).

Further, since the present compound also exhibited therapeutic effect of ABC-DLBCL on patients already having received standard treatment of NHL, it can also exhibit therapeutic effect on invalid cases of ABC-DLBCL in other anticancer agents defined in the present invention, including other Btk inhibitors.

The present invention can provide a medicament which can exert effect in treatment of ABC-DLBCL, irrespective of the presence or absence of CD79B mutation, which is recognized in a patient with ABC-DLBCL.

What is claimed is:

1. A method of treating B-cell non-Hodgkin's lymphoma comprising: administering to a human in need thereof a pharmaceutically effective amount of 6-amino-9-[(3R)-1-(2-butynoyl)-3-pyrrolidinyl]-7-(4-phenoxyphenyl)-7,9-dihydro-8H-purin-8-one or a salt thereof and at least one additional anticancer agent; wherein the at least one additional anticancer agent comprises a PI3K inhibitor, and wherein the PI3K inhibitor is CAL-101.

2. The method according to claim 1, wherein 6-amino-9-[(3R)-1-(2-butynoyl)-3-pyrrolidinyl]-7-(4-phenoxyphenyl)-7,9-dihydro-8H-purin-8-one or a salt thereof and the at least one additional anticancer agent are administered simultaneously.

3. The method according to claim 1, wherein 6-amino-9-[(3R)-1-(2-butynoyl)-3-pyrrolidinyl]-7-(4-phenoxyphenyl)-7,9-dihydro-8H-purin-8-one or a salt thereof is administered before the at least one additional anticancer agent.

4. The method according to claim 1, wherein 6-amino-9-[(3R)-1-(2-butynoyl)-3-pyrrolidinyl]-7-(4-phenoxyphenyl)-7,9-dihydro-8H-purin-8-one or a salt thereof is administered after the at least one additional anticancer agent.

5. The method according to claim 1, wherein B-cell non-Hodgkin's lymphoma is selected from the group consisting of Burkitt's lymphoma, AIDS-related lymphoma, marginal zone B-cell lymphoma selected from nodal marginal zone B-cell lymphoma, extranodal marginal zone B-cell lymphoma and splenic marginal zone B-cell lymphoma, diffuse large B-cell lymphoma, primary effusion lymphoma, lymphomatoid granulomatosis, follicular lymphoma, B-cell chronic lymphocytic leukemia, B-cell prolymphocytic leukemia, lymphoplasmacytic leukemia/Waldenstrom's macroglobulinemia, plasmacytoma, mantle cell lymphoma, mediastinal large B-cell lymphoma, intravascular large B-cell lymphoma and hairy cell leukemia.

6. The method according to claim 5, wherein diffuse large B-cell lymphoma is selected from the group consisting of activated B-cell like diffuse large B-cell lymphoma and germinal center B-cell like diffuse large B-cell lymphoma.

7. The method according to claim 6 wherein activated B-cell like diffuse large B-cell lymphoma is activated B-cell like diffuse large B-cell lymphoma which has been developed in a patient having CD79B wild-type or mutant gene background.

\* \* \* \* \*